United States Patent
Venugopal et al.

(10) Patent No.: US 12,125,217 B2
(45) Date of Patent: Oct. 22, 2024

(54) SYSTEM AND METHOD FOR DETECTING STENOSIS

(71) Applicant: GE PRECISION HEALTHCARE LLC, Wauwatosa, WI (US)

(72) Inventors: Prem Venugopal, Clifton Park, NY (US); Cynthia Elizabeth Landberg Davis, Niskayuna, NY (US); Jed Douglas Pack, Glenville, NY (US); Jhimli Mitra, Niskayuna, NY (US); Soumya Ghose, Niskayuna, NY (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 426 days.

(21) Appl. No.: 17/520,254

(22) Filed: Nov. 5, 2021

(65) Prior Publication Data

US 2023/0144624 A1   May 11, 2023

(51) Int. Cl.
| | | |
|---|---|---|
| *G06T 7/246* | (2017.01) | |
| *G06T 7/10* | (2017.01) | |
| *G16H 30/20* | (2018.01) | |

(52) U.S. Cl.
CPC ............... *G06T 7/248* (2017.01); *G06T 7/10* (2017.01); *G16H 30/20* (2018.01); *G06T 2207/30104* (2013.01)

(58) Field of Classification Search
CPC . G06T 7/248; G06T 7/10; G06T 2207/30104; G16H 30/20
See application file for complete search history.

(56) References Cited

U.S. PATENT DOCUMENTS

| | | |
|---|---|---|
| 8,526,699 B2 | 9/2013 | Mittal et al. |
| 9,349,178 B1 | 5/2016 | Itu et al. |
| 9,700,219 B2 | 7/2017 | Sharma et al. |
| 9,761,004 B2 | 9/2017 | Mittal et al. |
| 9,974,453 B2 | 5/2018 | Fonte et al. |
| 10,010,255 B2 | 7/2018 | Fonte et al. |
| 10,575,810 B2 | 3/2020 | Sankaran et al. |
| 11,301,994 B2 * | 4/2022 | Schmitt .................. G16H 50/50 |
| 2016/0066795 A1 * | 3/2016 | Grass ................... A61B 5/6851 |
| | | 600/407 |

(Continued)

OTHER PUBLICATIONS

Sharma, Puneet, et al.; "A Framework for Personalization of Coronary Flow Computations During Rest and Hyperemia", 34th Annual International Conference of IEEE EMBS, 2012; pp. 6665-6668.

(Continued)

*Primary Examiner* — Shefali D Goradia
(74) *Attorney, Agent, or Firm* — Fletcher Yoder P.C.

(57) ABSTRACT

A computer-implemented method includes obtaining, via a processor, segmented image patches of a vessel along a coronary tree path and associated coronary flow distribution for respective vessel segments in the segmented image patches. The method also includes determining, via the processor, a pressure drop distribution along an axial length of the vessel from the segmented image patches and the associated coronary flow distribution. The method further includes determining, via the processor, critical points in the pressure drop distribution. The method even further includes detecting, via the processor, a presence of a stenosis based on the critical points in the pressure drop distribution.

18 Claims, 6 Drawing Sheets

(56) References Cited

U.S. PATENT DOCUMENTS

2020/0281553 A1* 9/2020 Lavi ................ A61B 5/02007

OTHER PUBLICATIONS

Taylor, Charles A., et al.; "Computational Fluid Dynamics Applied to Cardiac Computed Tomography for Noninvasive Quantification of Fractional Flow Reserve", Journal of American College of Cardiology, vol. 61, No. 22, 2013; pp. 2233-2241.
Van der Horst, Arjen, et al.; "Towards Patient-Specific Modeling of Coronary Hemodynamics in Healthy and Diseased State", Computational and Mathematical Methods of Medicine, vol. 2013, Article ID 393792, accepted 2013; pp. 1-15.
Shahzad, Rahil, et al.; "Automatic segmentation, detection and quantification of coronary artery stenoses on CTA", Int J Cardiovasc Imaging (2013) 29; pp. 1847-1859.
iTu, Lucian, et al.; "A machine-learning approach for computation of fractional flow reserve from coronary computed tomography", J Appl Physiol 121: 2016; pp. 42-52.

* cited by examiner

SYSTEM AND METHOD FOR DETECTING STENOSIS

BACKGROUND

The subject matter disclosed herein relates to systems and methods for detecting stenosis.

Volumetric medical imaging technologies use a variety of techniques to gather three-dimensional information about the body. For example, computed tomography (CT) imaging system measure the attenuation of X-ray beams passed through a patient from numerous angles. Based upon these measurements, a computer is able to reconstruct images of the portions of a patient's body responsible for the radiation attenuation. As will be appreciated by those skilled in the art, these images are based upon separate examination of a series of angularly displaced measurements. It should be pointed out that a CT system produces data that represent the distribution of linear attenuation coefficients of the scanned object. The data are then reconstructed to produce an image that is typically displayed on a screen, and may be printed or reproduced on film.

For example, in the field of CT angiography (CTA), vasculature and other circulatory system structures may be imaged, typically by administration of a radio-opaque dye prior to imaging. Visualization of the CTA data typically is performed in a two-dimensional manner, i.e., slice-by-slice, or in a three-dimensional manner, i.e., volume visualization, which allows the data to be analyzed for vascular pathologies. For example, the data may be analyzed for aneurysms, vascular calcification, renal donor assessment, stent placement, vascular blockage, and vascular evaluation for sizing and/or runoff. Once a pathology is located, quantitative assessments of the pathology may be made of the on the original two-dimensional slices.

Atherosclerosis is a vascular disease in which cholesterol and other material accumulate along the inner lining of an artery forming atheromas or plaques. These plaque deposits, can over time, lead to a local narrowing of the blood vessel, often referred to as a stenosis. In the presence of a substantial stenosis, blood flow to the tissues downstream becomes severely restricted. Initially, severity of a stenosis was based purely on geometry, such as the percent reduction in lumen diameter. However, it was soon realized that anatomic significance of a stenosis did not always translate to functional significance. The concept of fractional flow reserve (FFR) was introduced to address this issue. It is defined as the ratio of pressure distal to the stenosis to the pressure proximal to it and measures the hemodynamic resistance of the stenosis relative to the resistance of the coronary microcirculation. Typically, FFR is measured at the time of invasive coronary angiography by inserting a tiny guide wire through a standard diagnostic catheter. A sensor at the tip of the wire measures pressure. Low values of FFR indicate a hemodynamically significant stenosis and clinical trials have demonstrated that intervention can be deferred when FFR>0.8.

Recently, model-based approaches for estimating FFR have been proposed. These approaches combine imaging data from CTA or invasive coronary angiography with Computational Fluid Dynamics (CFD) modeling to estimate FFR. In some of the proposed approaches a reduced-order model is used, for computational efficiency, as opposed to a 3D CFD model of the coronary vasculature. In these reduced-order model approaches, the large vessels (ascending aorta, coronary epicardial arteries, etc.) are modeled as axi-symmetric vessel segments and the blood flow dynamics in these vessels determined using the one-dimensional (1D) wave propagation equations. At stenosis locations, the equations are modified to account for the additional pressure drop introduced by the stenosis. In order to do this a priori detection of stenosis regions is needed. Besides blood flow modeling, detecting stenosis locations may be needed for reviewing the results of lumen segmentation in critical regions, interventional treatment planning, or performing risk stratification of patients.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a computer-implemented method is provided. The method includes obtaining, via a processor, segmented image patches of a vessel along a coronary tree path and associated coronary flow distribution for respective vessel segments in the segmented image patches. The method also includes determining, via the processor, a pressure drop distribution along an axial length of the vessel from the segmented image patches and the associated coronary flow distribution. The method further includes determining, via the processor, critical points in the pressure drop distribution. The method even further includes detecting, via the processor, a presence of a stenosis based on the critical points in the pressure drop distribution.

In another embodiment, a computer-implemented method is provided. The method includes obtaining, via a processor, segmented image patches of a vessel along a coronary tree path. The method also includes determining, via the processor, a cross-sectional area distribution along an axial length of the vessel from the segmented image patches. The method further includes determining, via the processor, critical points in the cross-sectional area distribution. The method even further includes detecting, via the processor, a presence of a stenosis based on the critical points in the cross-sectional area distribution.

In a further embodiment, a processor-based system is provided. The processor-based system includes a memory encoding one or more processor-executable routines. The routines, when executed cause acts to be performed. The acts include obtaining segmented image patches of a vessel along a coronary tree path. The acts also include determining a cross-sectional area distribution or a pressure drop distribution along an axial length of the vessel from at least the segmented image patches. The acts further include determining critical points in the cross-sectional area distribution or the pressure drop distribution. The acts even further include detecting a presence of a stenosis based on the critical points in the cross-sectional area distribution or the pressure drop distribution. The processor-based system also includes a processor configured to access and execute the one or more routines encoded by the memory.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
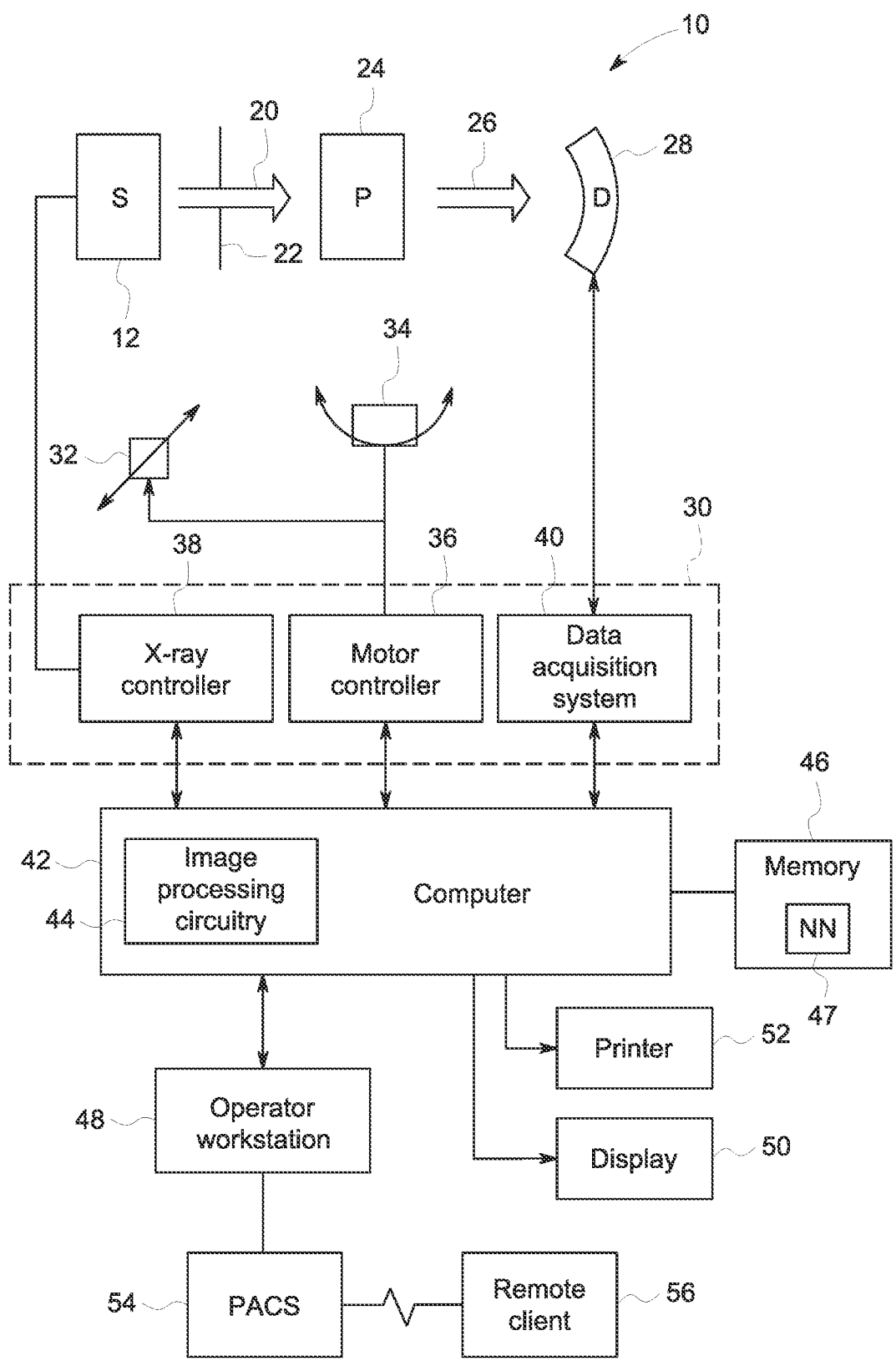
FIG. 1 is a schematic illustration of an embodiment of a computed tomography (CT) system configured to acquire CT images of a patient and process the images, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present disclosure provides systems and methods for detecting stenosis based on the vessel cross-sectional area distribution as well as the pressure drop distribution. Both methods first detect "peaks" (i.e., local maxima) and "valleys" (i.e., local minima) in the cross-sectional area distribution or pressure drop distribution as locations where the spatial derivative of a radius or a pressure drop with respect to the axial co-ordinate is zero. In the disclosed embodiments, a stenosis is detected as the presence of a valley in between two adjacent peaks in the case of cross-sectional area distribution or a peak between two adjacent valleys in the case of pressure drop distribution. Detecting stenosis in the cross-sectional area distribution occurs without having to estimate a hypothetical vessel radius. In certain embodiments, stenosis detection may occur utilizing both cross-sectional-area distribution and pressure drop distribution. The disclosed embodiments for stenosis detection may be useful for improving the results of lumen segmentation. For example, after performing lumen segmentation using an automated algorithm, the user may be shown the segmentation results in the stenosed regions and then, if needed, manually edit the segmentation. Further, stenosis detection may aid in the workflow in the cardiac catheterization lab. If the sizes and locations of stenosis are known, then decisions about the number and size of stents needed can be made a priori, thus, improving workflow. Even further, stenosis detection may aid in performing risk stratification of patients. For example, in determining plaque rupture risk, the forces acting on the plaque need to be quantified, thus, requiring the need for stenosis detection.

With the foregoing discussion in mind, FIG. 1 illustrates an embodiment of an imaging system 10 for acquiring and processing image data in accordance with aspects of the present disclosure. Although the following embodiments are discussed in terms of the computed tomography (CT) imaging system, the embodiments may also be utilized with other imaging systems (e.g., X-ray, PET, CT/PET, SPECT, nuclear CT, magnetic resonance imaging, etc.). In the illustrated embodiment, system 10 is a CT system designed to acquire X-ray projection data, to reconstruct the projection data into a tomographic image, and to process the image data for display and analysis. The CT imaging system 10 includes an X-ray source 12. As discussed in detail herein, the source 12 may include one or more X-ray sources, such as an X-ray tube or solid-state emission structures. The X-ray source 12, in accordance with present embodiments, is configured to emit an X-ray beam 20 at one or more energies.

In certain implementations, the source 12 may be positioned proximate to a collimator 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements. Each detector element produces an electrical signal that represents the intensity of the X-ray beam incident at the position of the detector element when the beam strikes the detector 28. Electrical signals are acquired and processed to generate one or more scan datasets or reconstructed images.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28 in accordance with the steps and processes discussed herein. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer may include processing circuitry 44 (e.g., image processing circuitry). The computer 42 may include or communicate with one or more non-transitory memory devices 46 that can store data processed by the computer 42, data to be processed by the computer 42, or instructions to be executed by a processor (e.g., processing circuitry 44) of the computer 42. For example, the processing circuitry 44 of the computer 42 may execute one or more sets of instructions stored on the memory 46, which may be a memory of the computer 42, a memory of the processor, firmware, or a similar instantiation. In accordance with present embodiments, the memory 46 stores sets of instructions that, when executed by the processor, perform image processing methods as discussed herein. The memory 46 also stores one or more algorithms and/or neural networks 47 that may be utilized in segmentation of vessels and detection of stenosis as described in greater detail below.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, to observe reconstructed images, to control imaging, and so forth. Additionally, the system 10 may include a printer 52 coupled to the operator workstation 48 and configured to print images. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Further, the computer 42 and operator workstation 48 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

While the preceding discussion has treated the various exemplary components of the imaging system 10 separately, these various components may be provided within a common platform or in interconnected platforms. For example, the computer 30, memory 38, and operator workstation 40 may be provided collectively as a general or special purpose computer or workstation configured to operate in accordance with the aspects of the present disclosure. In such embodiments, the general or special purpose computer may be provided as a separate component with respect to the data acquisition components of the system 10 or may be provided in a common platform with such components. Likewise, the system controller 30 may be provided as part of such a computer or workstation or as part of a separate system dedicated to image acquisition.

Figure 2:
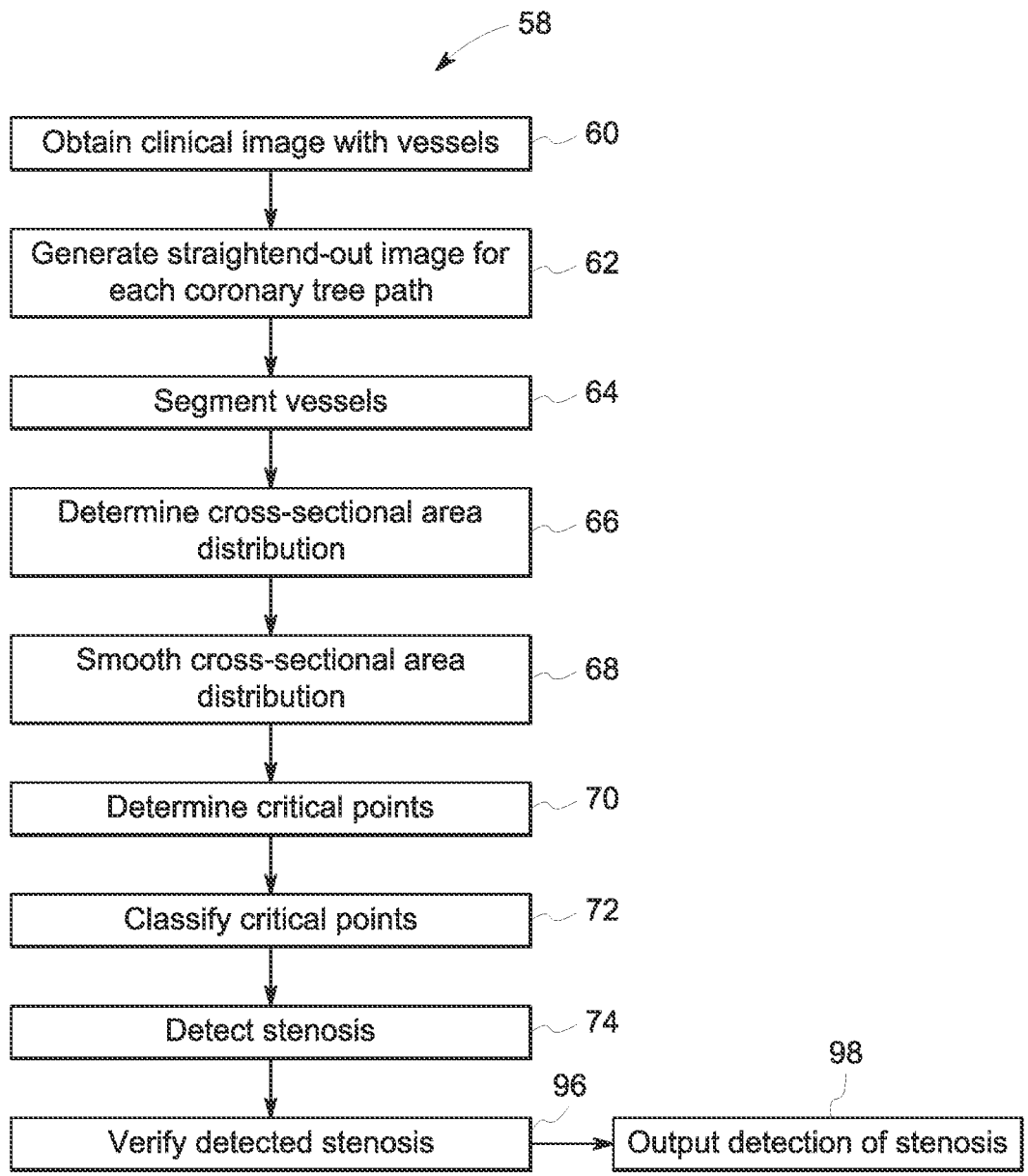
FIG. 2 is a flow chart of a method for detecting stenosis (e.g., utilizing cross-sectional area distribution), in accordance with aspects of the present disclosure.

FIG. 2 is a flow chart of a method 58 for detecting stenosis (e.g., utilizing cross-sectional area distribution). Some or all of the steps of the method 58 may be performed by the system controller 24, processing component 30, operator workstation 40, and/or a remote computing device. One or more steps of the illustrated method 58 may performed in a different order from the order depicted in FIG. 2 and/or simultaneously. The method 58 includes obtaining or receiving clinical images (e.g., 3D CTA images) with blood vessels (block 60). The method 58 also includes generating a straightened-out image for each coronary tree path within a respective clinical image (block 62). Vessel centerlines are determined along the coronary tree. Then, for each coronary tree path (a path here is defined as starting from the left or right coronary ostia and ending at a terminal point in the tree), the image normal to the vessel centerline is determined. This helps to transform each coronary tree path and the surrounding image from physical space to a straightened-out space.

The method 58 further includes segmenting the vessels that include each straightened-out coronary path (block 64). In certain embodiments, a trained deep learning algorithm is utilized to segment the vessels that include each straightened-out coronary path. In segmenting the vessels, segmented 3D image patches may be extracted.

The method 58 even further includes determining a cross-sectional area distribution (e.g., radius distribution) along each coronary path from the segmented vessels (block 66). To determine the cross-sectional area, the pixels within the segmented vessel at a given cross-sectional plane are summed up and multiplied by the cross-sectional area. The cross-sectional area is further converted into an equivalent radius, which is the radius of a circle with the same cross-sectional area. The cross-area distribution includes the equivalent radius at each axial location along an axial length of a vessel (e.g., coronary path). The cross-sectional area distribution may be noisy. Therefore, before proceeding further, the method 58 may include smoothing the cross-sectional area distribution to remove any high frequency noise (block 68).

The method 58 includes determining critical points in the smoothed out cross-sectional area distribution (block 70). The method 58 also includes determining or classifying each critical point as either a local maximum or a local minimum (block 72). Critical points (e.g., local maxima ("peaks") and local minima ("valleys")) in the smoothed out cross-sectional area distribution are determined via a derivative of the cross-sectional area distribution. The local maxima and local minima are locations where $$\frac{dr}{dz} = 0,$$

where r is the radius corresponding to the cross-sectional area and z is the axial co-ordinate along the coronary path. A second derivative of the cross-sectional area distribution is utilized in classification of the critical points as either a local maximum or a local minimum. Depending on the sign of $$\frac{d^2r}{dz^2},$$

a location with $$\frac{dr}{dz} = 0$$

is classified as a "peak" (i.e., local maximum) or "valley" (i.e., local minimum). If $$\frac{d^2r}{dz^2} < 0,$$

then the location is classified as a peak. If $$\frac{d^2r}{dz^2} > 0,$$

then the location is classified as valley. The derivatives $$\frac{dr}{dz} \text{ and } \frac{d^2r}{dz^2}$$

are computed via finite difference approximations.

Figure 3:
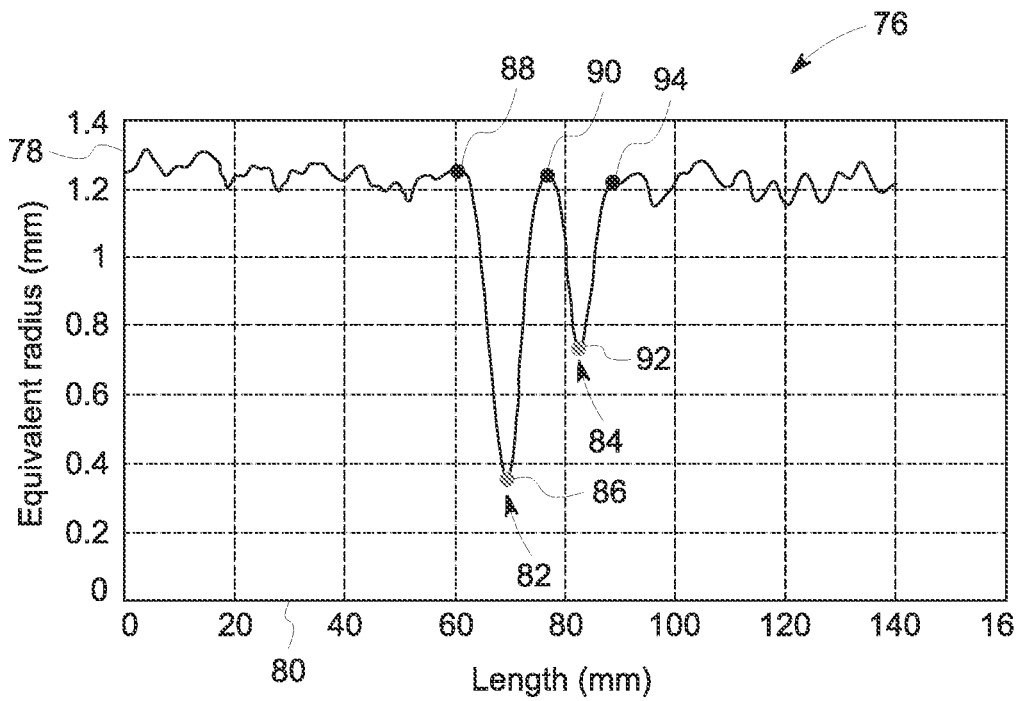
FIG. 3 is a graphical representation of a cross-sectional area distribution for a vessel (e.g., along a coronary tree path)

The method 58 also includes detecting a presence of stenosis in the cross-sectional area distribution based on the critical points (e.g., classified critical points) (block 74). FIG. 3 is a graphical representation 76 of a cross-sectional area distribution for a vessel (e.g., along a coronary tree path). The graphical representation 76 includes a Y-axis 78 representing the equivalent radius (corresponding to a cross-sectional area) and an X-axis 80 representing a length (e.g., axial length) of the vessel. If a valley is detected between two adjacent peaks, then the region between the two adjacent peaks is classified as a stenosis. Two side-by-side stenosis 82, 84 are detected in the cross-sectional area distribution. For stenosis 82, local minimum 86 is located between adjacent local maxima 88, 90. For stenosis 84, local minimum 92 is located between adjacent local maxima 90, 94. It is noted that detecting stenosis in the cross-sectional area distribution occurs without having to estimate a hypothetical vessel radius.

Returning to FIG. 2, the method 58 further includes verifying the detected stenosis (block 96). Verification of the stenosis may minimize having an excessive number of stenosis detected utilizing the method 58. Verification of the stenosis is described in greater detail below in FIGS. 4 and 5.

The method 58 still further includes outputting detection of the stenosis (block 98). The detection of the stenosis may be provided via providing a user-perceptible indication on an output device (e.g., monitor, computer, smart phone, etc.)

Besides the detection of the stenosis, additional information may be provided (e.g., associated measurements, location of the stenosis, etc.). The detection of the stenosis and related information may be recorded or stored in a memory/database.

Figure 4:
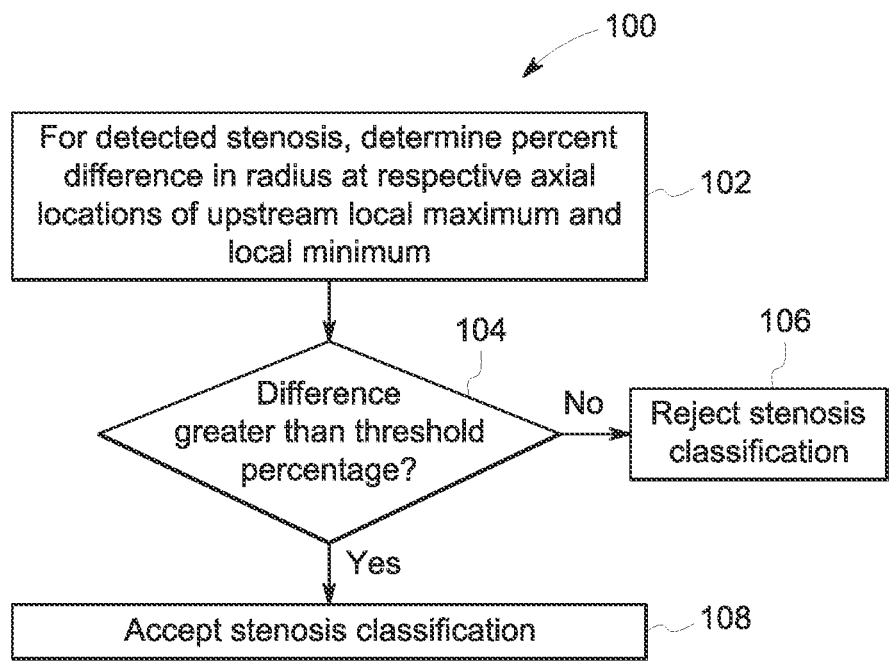
FIG. 4 is a flow chart of a method for verifying a detected stenosis, in accordance with aspects of the present disclosure.

An excessive number of stenosis may be detected utilizing the above approach. FIG. 4 is a flow chart of a method 100 for verifying a detected stenosis (to minimize the number of detected stenosis). Some or all of the steps of the method 100 may be performed by the system controller 24, processing component 30, operator workstation 40, and/or a remote computing device. One or more steps of the illustrated method 100 may performed in a different order from the order depicted in FIG. 4 and/or simultaneously. The method 100 includes, for each detected stenosis, determining a percent difference (e.g., percent stenosis) (block 102). Percent stenosis is defined as $$\frac{(r_{peaku} - r_{trough}) \times 100}{r_{peaku}},$$

where $r_{peaku}$ is the radius at the axial location of the upstream peak of the two adjacent peaks and $r_{trough}$ is the radius at the axial location of the trough or valley between the two adjacent peaks. For example, for the stenosis 82 in FIG. 3, the percent difference (e.g., percent stenosis) is determined utilizing the radius at local maximum 88 and the radius at the local minimum 86.

The method 100 also includes determining if the percent difference (e.g., percent stenosis) is greater than a threshold percentage or cut-off percentage (e.g., percent stenosis threshold) (block 104). For example, in certain embodiments, the threshold percentage may be 30 percent. In other embodiments, the threshold percentage may be a different value (e.g., 25, 26, 27, 28, 29, 31, 32, 33, 34, or 35 percent or another value). If the percent difference is not greater than the threshold percentage, the method 100 includes rejecting the classification of the detected region as a stenosis (block 106). If the percent difference is greater than the threshold percentage, the method 100 includes accepting the classification of the detected region as a stenosis (block 108).

Figure 5:
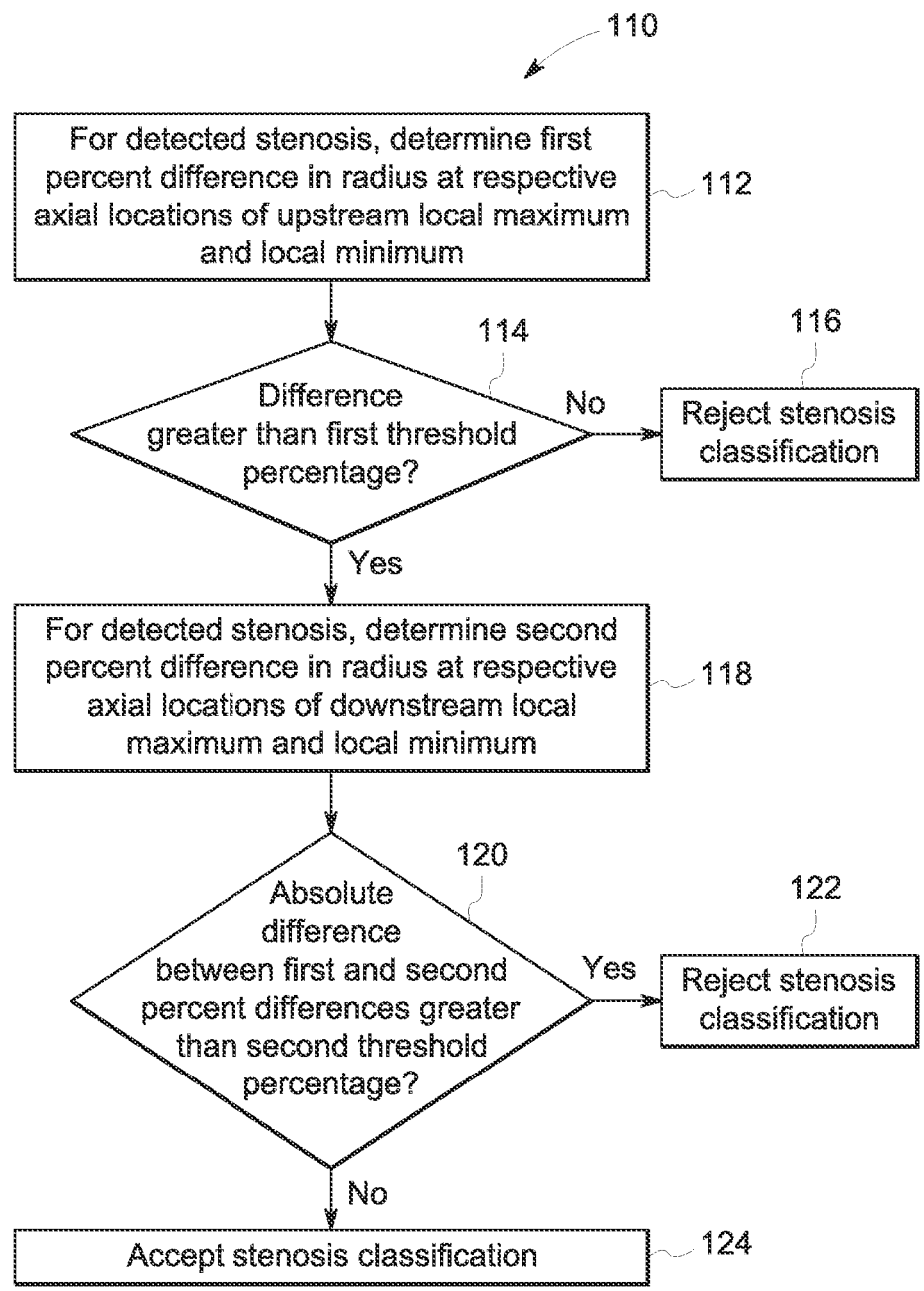
FIG. 5 is a flow chart of a method for verifying a detected stenosis (e.g., to rule out bifurcation of a vessel), in accordance with aspects of the present disclosure.

Sometimes when a large vessel branches off into a small vessel, the bifurcation region could be identified as a stenosis with this approach. FIG. 5 is a flow chart of a method 110 for verifying a detected stenosis (e.g., to rule out bifurcation of a vessel). Some or all of the steps of the method 110 may be performed by the system controller 24, processing component 30, operator workstation 40, and/or a remote computing device. One or more steps of the illustrated method 110 may performed in a different order from the order depicted in FIG. 5 and/or simultaneously. Blocks 112, 114, and 116 of the method 110 are the same as the blocks 102, 104, and 106 in the method 110.

The method 110 includes for each detected stenosis, determining an additional percent difference (e.g., percent stenosis) (block 118). However, the additional percent difference is defined as $$\frac{(r_{peakd} - r_{trough}) \times 100}{r_{peakd}},$$

where $r_{peakd}$ is the radius at the axial location of the downstream peak of the two adjacent peaks and $r_{trough}$ is the radius at the axial location of the trough or valley between the two adjacent peaks. For example, for the stenosis 82 in FIG. 3, the additional percent difference is determined utilizing the radius at local maximum 94 and the radius at the local minimum 86.

Returning to FIG. 5, the method 110 also includes determining if the absolute percent difference between the percent stenosis (e.g., determined in block 112) and the additional percent difference (e.g., determined in block 118) is greater than another threshold percentage or cut-off percentage (block 120). For example, in certain embodiments, the threshold percentage may be 15 percent. In other embodiments, the threshold percentage may be a different value (e.g., 10, 11, 12, 13, 14, 16, 17, 18, 19, or 20 percent or another value). If the absolute percent difference is greater than the additional threshold percentage, the method 110 includes rejecting the classification of the detected region as a stenosis due to potential vessel bifurcation (block 122). If the absolute percent difference is not greater than the additional threshold percentage, the method 110 includes accepting the classification of the detected region as a stenosis (block 124).

Figure 6:
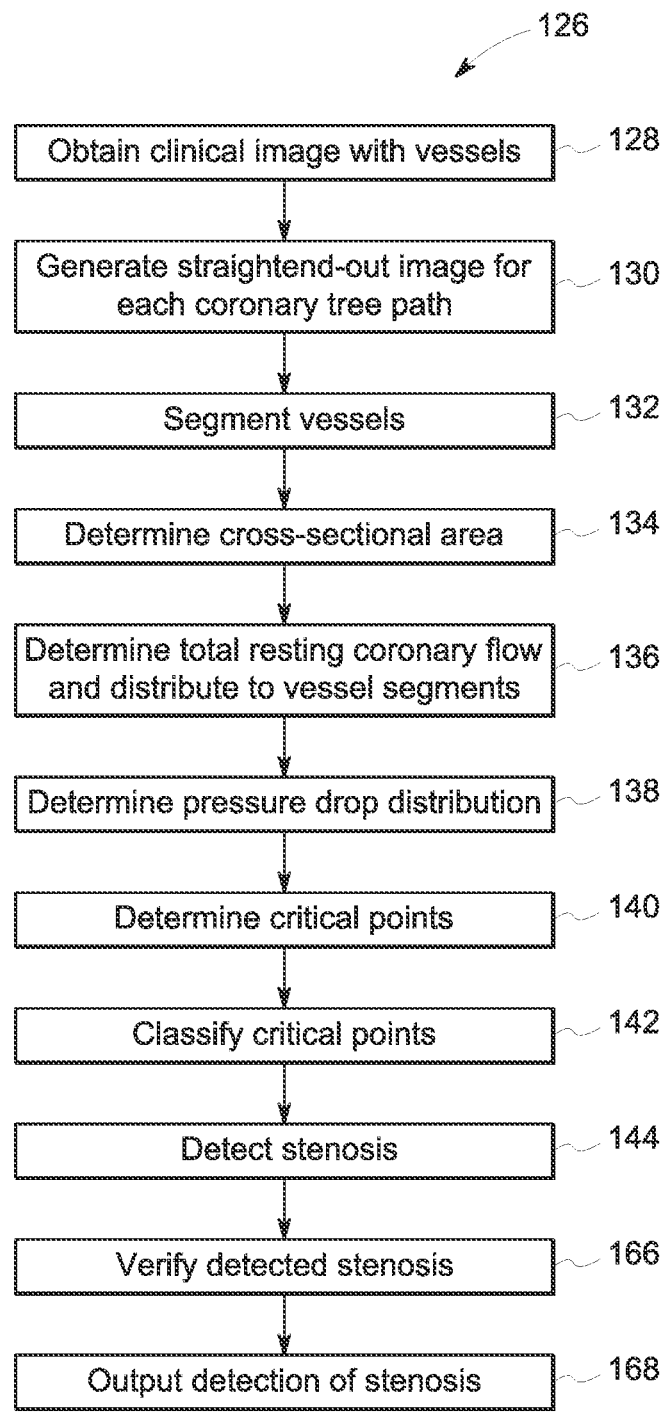
FIG. 6 is a flow chart of a method for detecting stenosis (e.g., utilizing pressure drop distribution), in accordance with aspects of the present disclosure.

In the method 58, it was decided whether to accept or reject a stenosis solely based on a percent stenosis threshold. The method 58 does not consider absolute vessel radius in making this determination, which is important for determining functional significance. For example, a 30 percent stenosis in a small vessel may have greater functional significance than a 30 percent stenosis in a large vessel. Utilizing pressure drop avoids this issue. FIG. 6 is a flow chart of a method 126 for detecting stenosis (e.g., utilizing pressure drop distribution). Some or all of the steps of the method 126 may be performed by the system controller 24, processing component 30, operator workstation 40, and/or a remote computing device. One or more steps of the illustrated method 126 may performed in a different order from the order depicted in FIG. 6 and/or simultaneously. The method 126 includes obtaining or receiving clinical images (e.g., 3D CTA images) with blood vessels (block 128). The method 126 also includes generating a straightened-out image for each coronary tree path within a respective clinical image (block 130). Vessel centerlines are determined along the coronary tree. Then, for each coronary tree path (a path here is defined as starting from the left or right coronary ostia and ending at a terminal point in the tree), the image normal to the vessel centerline is determined. This helps to transform each coronary tree path and the surrounding image from physical space to a straightened-out space.

The method 126 further includes segmenting the vessels that include each straightened-out coronary path (block 132). In certain embodiments, a trained deep learning algorithm is utilized to segment the vessels that include each straightened-out coronary path. In segmenting the vessels, segmented 3D image patches may be extracted.

The method 126 includes determining a cross-sectional area along each coronary path from the segmented vessels (block 134). The method 126 also includes determining the total resting coronary flow and distributing it to the individual vessel segments (block 136).

The method 126 even further includes determining a pressure drop distribution along each coronary path from the cross-sectional area and the associated coronary flow distribution for the respective vessel segments (block 138). The pressure drop distribution includes a pressure drop at each axial location along an axial length of a vessel (e.g., coronary path). With the cross-sectional area and flow distribution known, a 1D model (without the additional stenosis loss term) is used to determine the pressure drop distribution for each coronary path as follows:

$$\Delta p = 8\pi\mu \int_{z_1}^{z_2} \frac{Q}{A^2} dz. \quad (1)$$

Here, $\Delta p$ is the pressure drop between axial locations $z_1$ and $z_2$, Q is the volume flow rate, $\mu$ is the blood flow viscosity, and A is the vessel cross-sectional area. Even without the additional loss term, there will be a small increase followed by a decrease in $\Delta p$ in regions of stenosis which is utilized in detecting the stenosis.

The method 126 includes determining critical points in the pressure drop distribution (block 140). The method 126 also includes determining or classifying each critical point as either a local maximum or a local minimum (block 142). Critical points (e.g., local maxima ("peaks") and local minima ("valleys")) in the pressure drop distribution are determined via a derivative of the pressure drop distribution. The local maxima and local minima are locations where $$\frac{d\Delta p}{dz} = 0,$$

where $\Delta p$ us the pressure drop and z is the axial co-ordinate along the coronary path. A second derivative of the pressure drop distribution is utilized in classification of the critical points as either a local maximum or a local minimum. Depending on the sign of $$\frac{d^2\Delta p}{dz^2},$$

a location with $$\frac{d\Delta p}{dz} = 0$$

is classified as a "peak" (i.e., local maximum) or "valley" (i.e., local minimum). If $$\frac{d^2\Delta p}{dz^2} < 0,$$

then the location is classified as a peak. If $$\frac{d^2\Delta p}{dz^2} > 0,$$

then the location is classified as valley. The derivatives, $$\frac{d\Delta p}{dz} \text{ and } \frac{d^2\Delta p}{dz^2},$$

are computed via finite difference approximations.

Figure 7:
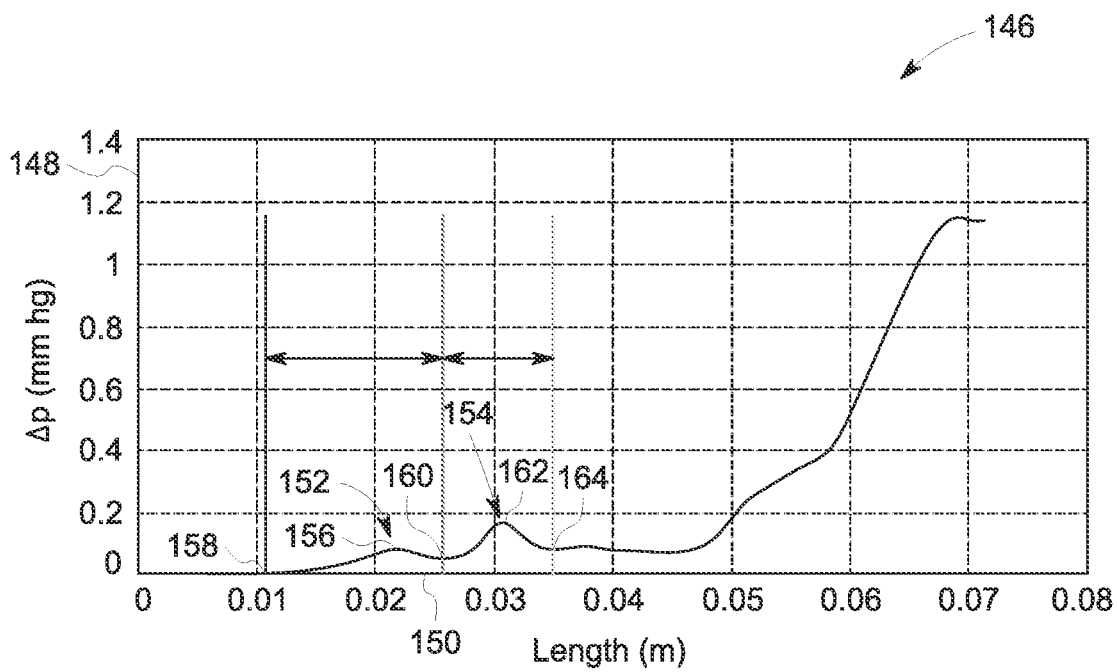
FIG. 7 is a graphical representation of a pressure drop distribution for a vessel (e.g., along a coronary tree path)

The method 126 also includes detecting a presence of stenosis in the pressure drop distribution based on the critical points (e.g., classified critical points) (block 144). FIG. 7 is a graphical representation 146 of a pressure drop distribution for a vessel (e.g., along a coronary tree path). The graphical representation 146 includes a Y-axis 148 representing the pressure drop and an X-axis 150 representing a length (e.g., axial length) of the vessel. If a peak is detected between two adjacent valleys, then the region between the two adjacent peaks is classified as a stenosis. Two side-by-side stenosis 152, 154 are detected in the pressure drop distribution. For stenosis 152, local maximum 156 is located between adjacent local minima 158, 160. For stenosis 154, local maximum 162 is located between adjacent local minima 160, 164.

Returning to FIG. 6, the method 126 further includes verifying the detected stenosis (block 166). Verification of the stenosis may minimize having an excessive number of stenosis detected utilizing the method 126. Verification of the stenosis is described in greater detail below in FIG. 8.

The method 126 still further includes outputting detection of the stenosis (block 168). The detection of the stenosis may be provided via providing a user-perceptible indication on an output device (e.g., monitor, computer, smart phone, etc.) Besides the detection of the stenosis, additional information may be provided (e.g., associated measurements, location of the stenosis, etc.). The detection of the stenosis and related information may be recorded or stored in a memory/database.

Figure 8:
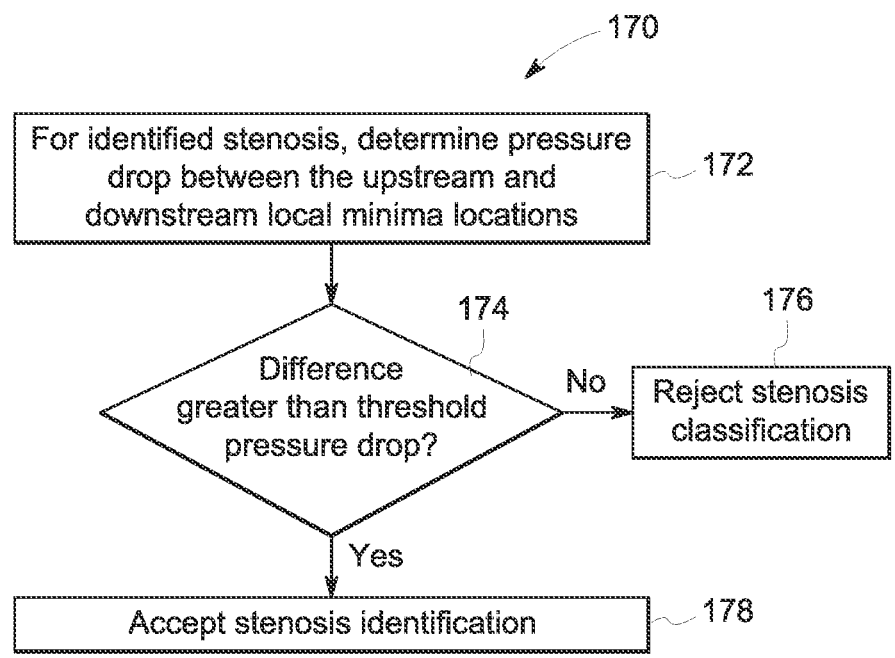
FIG. 8 is a flow chart of a method for verifying a detected stenosis, in accordance with aspects of the present disclosure.

An excessive number of stenosis may be detected utilizing the above approach. FIG. 8 is a flow chart of a method 170 for verifying a detected stenosis (to minimize the number of detected stenosis). Some or all of the steps of the method 170 may be performed by the system controller 24, processing component 30, operator workstation 40, and/or a remote computing device. One or more steps of the illustrated method 170 may performed in a different order from the order depicted in FIG. 8 and/or simultaneously. The method 170 includes, for each detected stenosis, determining the pressure across the stenosis (block 172). This pressure drop may be determined as $$\Delta p = 8\pi\mu \int_{z_{troughu}}^{z_{troughd}} \frac{Q}{A^2} dz,$$

where $z_{troughu}$ and $z_{troughd}$ are the axial locations of the upstream and downstream valleys of the detected stenosis. For example, for the stenosis 152 in FIG. 7, the pressure drop is computed between the local minima locations 158 and 160.

The method 170 also includes determining if the pressure drop is greater than a threshold pressure drop or cut-off pressure drop (block 174). For example, in certain embodiments, the threshold pressure drop may be 1 mm Hg. In other embodiments, the threshold pressure drop may be a different value (e.g., 0.5, 2, 3, or 4 mm Hg or another value). If the pressure drop is not greater than the threshold pressure drop, the method 170 includes rejecting the classification of the detected region as a stenosis (block 176). If the pressure drop is greater than the threshold pressure drop, the method 170 includes accepting the classification of the detected region as a stenosis (block 178). Method 100 based on a cut-off threshold for the percent stenosis can be used to further reduce the number of detected stenoses.

Technical effects of the disclosed subject matter include providing systems and methods for detecting stenosis based on the vessel cross-sectional area distribution and/or the pressure drop distribution. The disclosed embodiments for stenosis detection may be useful for improving the results of lumen segmentation. For example, after performing lumen segmentation using an automated algorithm, the user may be shown the segmentation results in the stenosed regions and then, if needed, manually edit the segmentation. Further, stenosis detection may aid in the workflow in the cardiac catheterization lab. If the sizes and locations of stenosis are known, then decisions about the number and size of stents needed can be made a priori, thus, improving workflow. Even further, stenosis detection may aid in performing risk stratification of patients. For example, in determining plaque rupture risk, the forces acting on the plaque need to be quantified, thus, requiring the need for stenosis detection.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method, comprising:
   obtaining, via a processor, a clinical image with vessels;
   generating, via the processor, a straightened-out image for a coronary tree path within the clinical image;
   obtaining, via the processor, segmented image patches of a vessel along the coronary tree path and associated coronary flow distribution for respective vessel segments in the segmented image patches;
   determining, via the processor, a pressure drop distribution along an axial length of the vessel from the segmented image patches and the associated coronary flow distribution;
   determining, via the processor, critical points in the pressure drop distribution based on a derivative of the pressure drop distribution;
   detecting, via the processor, a presence of a stenosis based on the critical points in the pressure drop distribution; and
   providing, via the processor, a user-perceptible indication on a user device of the presence of a stenosis when detected.

2. The computer-implemented method of claim 1, wherein the pressure drop distribution comprises a pressure drop at each axial location along the axial length of the vessel.

3. The computer-implemented method of claim 1, comprising determining, via the processor, whether each critical point is either a local minimum or a local maximum.

4. The computer-implemented method of claim 3, wherein detecting the presence of the stenosis comprises detecting the local maximum between two adjacent local minima.

5. The computer-implemented method of claim 4, comprising verifying, via the processor, the presence of the stenosis by:
   determining the pressure drop across the stenosis between the two adjacent local minima;
   comparing the pressure drop to a threshold pressure drop; and
   confirming the presence of the stenosis when the pressure drop is greater than the threshold pressure drop.

6. A computer-implemented method, comprising:
   obtaining, via a processor, a clinical image with vessels;
   generating, via the processor, a straightened-out image for a coronary tree path within the clinical image;
   obtaining, via the processor, segmented image patches of a vessel along the coronary tree path;
   determining, via the processor, a cross-sectional area distribution along an axial length of the vessel from the segmented image patches;
   determining, via the processor, critical points in the cross-sectional area distribution based on a derivate of the cross-sectional area distribution;
   detecting, via the processor, a presence of a stenosis based on the critical points in the cross-sectional area distribution; and
   providing, via the processor, a user-perceptible indication on a user device of the presence of a stenosis when detected.

7. The computer-implemented method of claim 6, wherein the cross-sectional area distribution comprises a radius of a cross-sectional area at each axial location along the axial length of the vessel.

8. The computer-implemented method of claim 6, comprising determining, via the processor, whether each critical point is either a local minimum or a local maximum.

9. The computer-implemented method of claim 8, wherein detecting the presence of the stenosis comprises detecting the local minimum between two adjacent local maxima.

10. The computer-implemented method of claim 9, comprising verifying, via the processor, the presence of the stenosis by:
    determining a first percent difference in radius between a first radius at a first axial location of an upstream local maximum of the two adjacent local maxima and a second radius at a second axial location of the local minimum;
    comparing the first percent difference to a first threshold percentage; and
    confirming the presence of the stenosis when the first percent difference is greater than the first threshold percentage.

11. The computer-implemented method of claim 10, comprising further verifying, via the processor, the presence of the stenosis is not due to a bifurcation region in the vessel by:
    determining a second percent difference in radius between a third radius at a third axial location of a downstream local maximum of the two adjacent local maxima and the second radius at the second axial location of the local minimum;
    determining a third percent difference between the first percent difference and the second percent difference;
    comparing the third percent difference to a second threshold percentage; and
    confirming the presence of the stenosis when the third percent difference is greater than the second threshold percentage.

12. A processor-based system, comprising:
    a memory encoding one or more processor-executable routines, wherein the routines, when executed cause acts to be performed comprising:
       obtaining a clinical image with vessels;
       generating a straightened-out image for a coronary tree path within the clinical image;
       obtaining segmented image patches of a vessel along the coronary tree path;
       determining a cross-sectional area distribution or a pressure drop distribution along an axial length of the vessel from at least the segmented image patches;
       determining critical points in the cross-sectional area distribution based on a derivative of the cross-sectional area distribution or the pressure drop distribution based on a derivative of the pressure drop distribution;
       detecting a presence of a stenosis based on the critical points in the cross-sectional area distribution or the pressure drop distribution; and
       providing a user-perceptible indication on a user device of the presence of a stenosis when detected; and
    a processor configured to access and execute the one or more routines encoded by the memory.

13. The processor-based system of claim 12, wherein the routines, when executed cause acts to be performed comprising:
    determining both the cross-sectional area distribution and the pressure drop distribution along the axial length of the vessel from at least the segmented image patches;
    determining the critical points in both the cross-sectional area distribution and the pressure drop distribution; and
    detecting the presence of the stenosis based on the critical points in both the cross-sectional area distribution and the pressure drop distribution.

14. The processor-based system of claim 12, wherein the routines, when executed cause acts to be performed comprising determining whether each critical point is either a local minimum or a local maximum.

15. The processor-based system of claim 14, wherein detecting the presence of the stenosis comprises detecting the local minimum between two adjacent local maxima in the cross-sectional area distribution.

16. The processor-based system of claim 14, wherein detecting the presence of the stenosis comprises detecting the local maximum between two adjacent local minima in the pressure drop distribution.

17. The processor-based system of claim 12, wherein the routines, when executed cause acts to be performed comprising:
    obtaining associated coronary flow distribution for respective vessel segments in the segmented image patches;
    determining the pressure drop distribution along the axial length of the vessel from the segmented image patches and the associated coronary flow distribution;
    determining the critical points in the pressure drop distribution; and
    detecting the presence of the stenosis based on the critical points in the pressure drop distribution.

18. The processor-based system of claim 12, wherein the routines, when executed cause acts to be performed comprising:
- determining the cross-sectional area distribution along the axial length of the vessel from the segmented image patches;
- determining the critical points in the cross-sectional area distribution; and
- detecting the presence of the stenosis based on the critical points in the cross-sectional area distribution.

* * * * *